(12) United States Patent
Armbruster et al.

(10) Patent No.: US 8,030,519 B2
(45) Date of Patent: Oct. 4, 2011

(54) METHOD FOR PRODUCING ACETOACETIC ACID ARYLAMIDES

(75) Inventors: Erich Armbruster, Naters (CH); Thuy Quach, Glis (CH); Günther Rosenthal, Brig (CH); Brian Schwegler, Visp (CH)

(73) Assignee: Lonza AG, Basel (CH)

(*) Notice: Subject to any disclaimer, the term of this patent is extended or adjusted under 35 U.S.C. 154(b) by 561 days.

(21) Appl. No.: 11/918,223

(22) PCT Filed: Apr. 12, 2006

(86) PCT No.: PCT/EP2006/003368
§ 371 (c)(1),
(2), (4) Date: Jan. 22, 2009

(87) PCT Pub. No.: WO2006/108632
PCT Pub. Date: Oct. 19, 2006

(65) Prior Publication Data
US 2009/0227811 A1    Sep. 10, 2009

(30) Foreign Application Priority Data
Apr. 12, 2005  (EP) ..................................... 05008038

(51) Int. Cl.
*C07C 231/04*  (2006.01)
*C07C 235/80*  (2006.01)

(52) U.S. Cl. ........................................................ 564/200
(58) Field of Classification Search ........................ None
See application file for complete search history.

(56) References Cited

U.S. PATENT DOCUMENTS

| 5,523,486 A | 6/1996 | Mack et al. |
| 6,586,631 B1 | 7/2003 | Balmer et al. |

FOREIGN PATENT DOCUMENTS

| DE | 2519036 | 11/1976 |
| EP | 0648738 | 4/1995 |
| EP | 0945430 | 9/1999 |

OTHER PUBLICATIONS

Ullmann's Encyclopedia Of Industrial Chemistry, 5$^{th}$ Ed., vol. 15, p. 71, (1990).

*Primary Examiner* — Brian J Davis
(74) *Attorney, Agent, or Firm* — Fisher, Christen & Sabol

(57) ABSTRACT

Acetoacetic acid arylamides are continuously produced from diketene and primary or secondary aromatic amines under the conditions of a reactive distillation in the presence of water. The continuous method provides a high purity of the products, nearly quantitative yields and a high rate of throughput.

18 Claims, 2 Drawing Sheets

METHOD FOR PRODUCING ACETOACETIC ACID ARYLAMIDES

This application is a 371 national stage patent application of International Patent Application No. PCT/EP2006/003368, filed on Apr. 12, 2006, that has priority benefit of European Patent Application No. 05008038.1, filed on Apr. 12, 2005.

The invention concerns a continuous process for the production of arylamides of acetoacetic acid from diketene and primary or secondary aromatic amines.

Arylamides of acetoacetic acid are important starting materials for the manufacture of dyes and pigments, but are also used in the manufacture of agrochemical agents (see e.g. Ullmann's Encyclopedia of Industrial Chemistry, 5$^{th}$ Ed., Vol. 15, p. 71).

The synthesis of arylamides of acetoacetic acid has been known for a long time and is based on the reaction of diketene with the respective aromatic amines in various organic and/or aqueous solvents and solvent mixtures (Ullmann's Encyclopedia of Industrial Chemistry, 5$^{th}$ Ed., Vol. 15, p. 71).

As a rule, the process is operated discontinuously in water or aqueous solutions.

Accordingly, DE-A-25 19 036 discloses the Production of various arylamides of acetoacetic acid by simultaneous metered addition of diketene and the respective aromatic amine in the presence of water or aqueous solutions. The resulting arylamide of acetoacetic acid is cooled in the reaction medium and allowed to crystallize. After centrifugation and drying, the arylamides of acetoacetic acid are obtained in good yield and high purity.

In addition, a continuous process for the manufacture of arylamides of acetoacetic acid is known from EP-A-0 648 738. Therein, diketene is continuously reacted with the aromatic amine in a mixture of water and alcohol, the residence time of the reaction mixture in the reactor being as long as possible. The resulting arylamide of acetoacetic acid is obtained by crystallization of the product stream discharged from the reactor.

A process for the production of water-containing arylamides of acetoacetic acid, whereby a two-phase system of molten product and an aqueous phase is formed in the course of the reaction, is disclosed in EP-A-0 945 430. The process is suitable for batchwise, semicontinuous or continuous operation and affords sufficiently pure products in good yields, however it requires rather long residence times and—because of the strongly exothermic reaction—in relation to the throughput relatively large reactor volumes ("hold up"). Consequently, in a tubular reactor of 10 cm diameter product throughputs of only about 1.5 kg/h were achieved. Moreover, the process requires relatively large amounts of water and an excess of diketene, in order to compensate losses due to side reactions and subsequent reactions. The object of the present invention was therefore to make available an alternative process that also provides pure products in excellent yield and that is particularly suitable for continuous operation at high throughputs and gets by with nearly stoichiometric amounts of diketene.

According to the invention this object has been achieved by conducting the reaction of diketene and aromatic amine in the manner of a reactive distillation in the presence of water. The heat of reaction is thereby absorbed by the evaporation of water and dissipated over the condenser. Since ideally no byproducts are formed in the reaction, no equilibrium between starting materials and product is reached, the product is less volatile than the starting materials diketene and aromatic amine and is therefore collecting as bottom product, and the head condensate essentially consists of the water added and the reflux ratio may thus be very high, it is not a reactive distillation in a strict sense. However, the usable apparatuses largely correspond to those used in classical reactive distillations, which is why the expression "in the manner of a reactive distillation" is being used herein. In particular, this is to be understood to mean that a chemical reaction in the liquid phase and a thermal mass transfer between the liquid phase and a countercurrent vapor phase are taking place simultaneously.

The process according to the invention is generally suited to the production of all arylamides of acetoacetic acid which, at the customary reaction temperatures, are liquids or forming liquid melts with water.

Preferably, the arylamides of acetoacetic acid obtainable according to the invention have the general formula

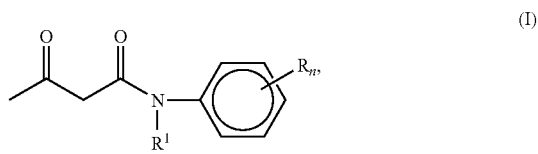

wherein R$^1$ is hydrogen or C$_{1-6}$ alkyl, n is an integer from 0 to 5, and the substituents R, if present, are equal or different and selected from the group consisting of C$_{1-6}$ alkyl groups, C$_{1-6}$ alkoxy groups and halogen atoms.

C$_{1-6}$ alkyl groups are herein to be understood to include all linear or branched alkyl groups having 1 to 6 carbon atoms, in particular methyl, ethyl, n-propyl, isopropyl, n-butyl, isobutyl, sec-butyl, tert-butyl, n-pentyl, isopentyl, tert-pentyl, neopentyl, n-hexyl and so on. A preferred alkyl is methyl. C$_{1-6}$ alkoxy groups are to be understood to include the groups composed of the above mentioned C$_{1-6}$ alkyl groups and oxygen, methoxy being preferred here. This applies accordingly to the expressions "C$_{1-4}$ alkyl" and "C$_{1-4}$ alkoxy" which are formed analogously. "Halogen" stands for fluorine, chlorine, bromine or iodine, preferably for chlorine.

Particularly preferred is the production of those arylamides of acetoacetic acid of formula I wherein R$^1$ is hydrogen.

Likewise particularly preferred is the production of those arylamides of acetoacetic acid of formula I wherein n is an integer from 0 to 3 and the substituents R, if present, are independently selected from the group consisting of C$_{1-4}$ alkyl groups, C$_{1-4}$ alkoxy groups and chlorine.

Especially preferred arylamides of acetoacetic acid are derived from aniline (n=0), o-anisidine (n=1; R=o-methoxy), o-toluidine (n=1; R=o-methyl), the xylidines (n=2; R=methyl), o-chloroaniline (n=1; R=o-Cl), 2,4-dimethoxyaniline (n=2; R=2,4-dimethoxy), 4-iso-propylaniline (n=1; R=p-isopropyl), 4-ethoxyaniline (n=1; R=p-ethoxy), 2,5-dimethoxy-aniline (n=2; R=2,5-dimethoxy) and 4-chloro-2,5-dimethoxyaniline (n=3; R=4-Cl, 2,5-dimethoxy).

By selecting an appropriate pressure the temperature of vaporization of water, and thus, the reaction temperature can be maintained within the range that is most suited to the respective product. The reaction temperature is suitably selected so that the product is obtained in liquid form, but exposed to minimum thermal stress. The process of the invention is preferably performed under reduced pressure.

Particularly suited for performing the process of the invention are plate columns, such as slit tray columns exhibiting low pressure drop. However, it is also possible to use packed columns.

In a particularly preferred embodiment two columns are used, whereby the actual reaction takes place in one column while in the other column the bottom product of the first column is stripped with water vapor to remove excess starting materials and other volatile impurities such as acetone.

The arylamides of acetoacetic acid prepared according to the invention are obtained in form of a water-containing melt. This melt can be converted into solid forms, such as pastilles, flakes or prills, using methods customary in the art. The dimension and size of said forms depends on the design of the pastillizing, flaking or prilling processes and may vary over a wide range. The arylamides of acetoacetic acid thus obtained exhibit particularly good flowability and an advantageous dissolution behavior. If an anhydrous product is desired, an arylamide of acetoacetic acid obtained according to the invention may be dried in a conventional way.

DESCRIPTION OF THE DRAWINGS

The drawings have a merely exemplary character and are not to be construed as limitations.

Figure 1:
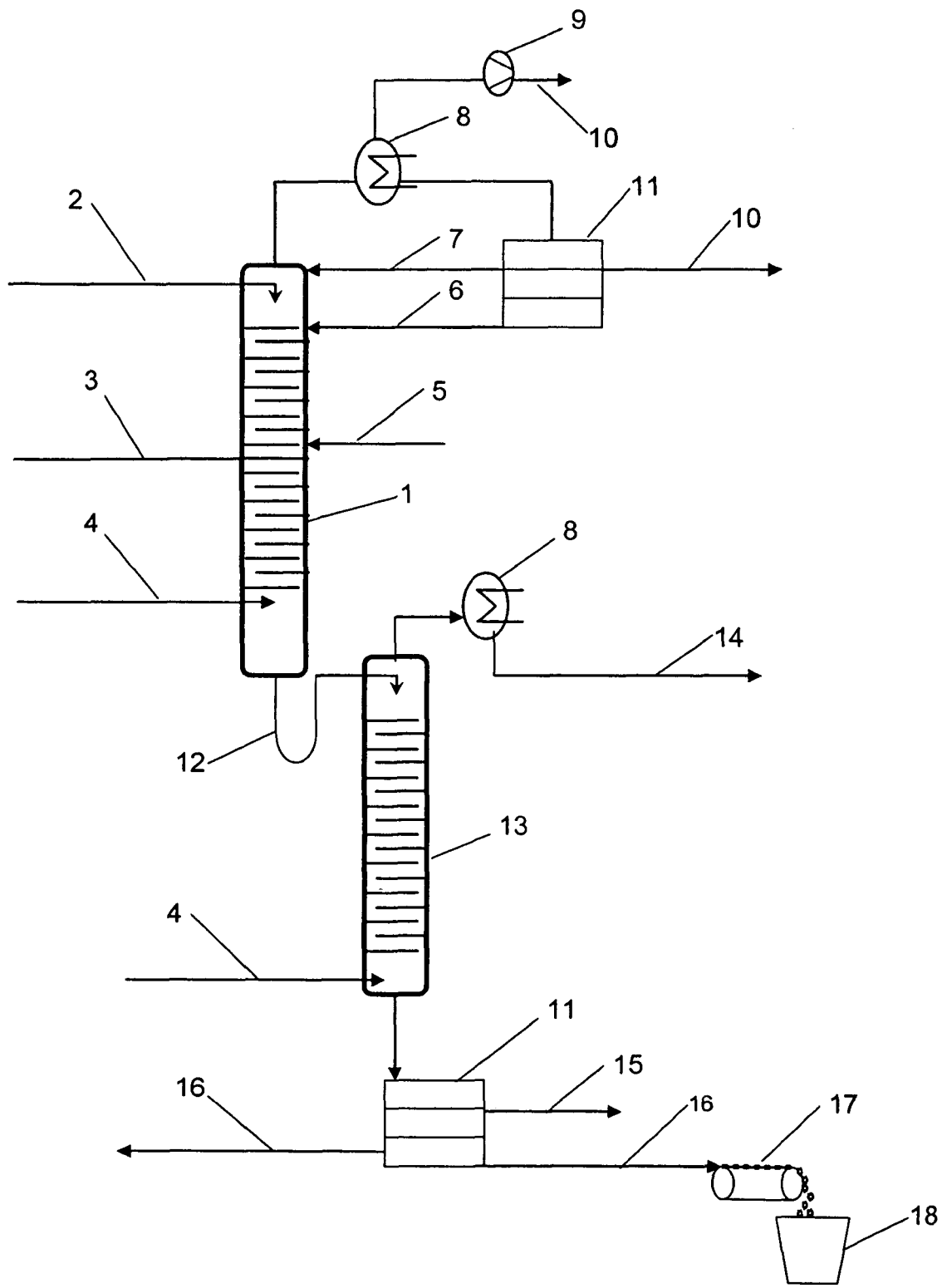
FIG. 1 depicts an apparatus for the process of the invention with two columns. In detail, the reference numerals have the meanings identified below:
1 Reaction column
2 Aniline feed line
3 Diketene feed line
4 Steam feed line
5 Water feed line
6 Condensate return, organic (heavy) phase
7 Condensate return, water phase
8 Condenser
9 Vacuum pump
10 Off-gas (to off-gas treatment)
11 Phase separator
12 Bottom product to stripping column
13 Stripping column
14 Condensate drain conduit (to wastewater treatment)
15 Water phase drain conduit (to wastewater treatment)
16 Product discharge (liquid)
17 Crystallizing belt ("flaker")
18 Receiver for solidified product
Figure 2:
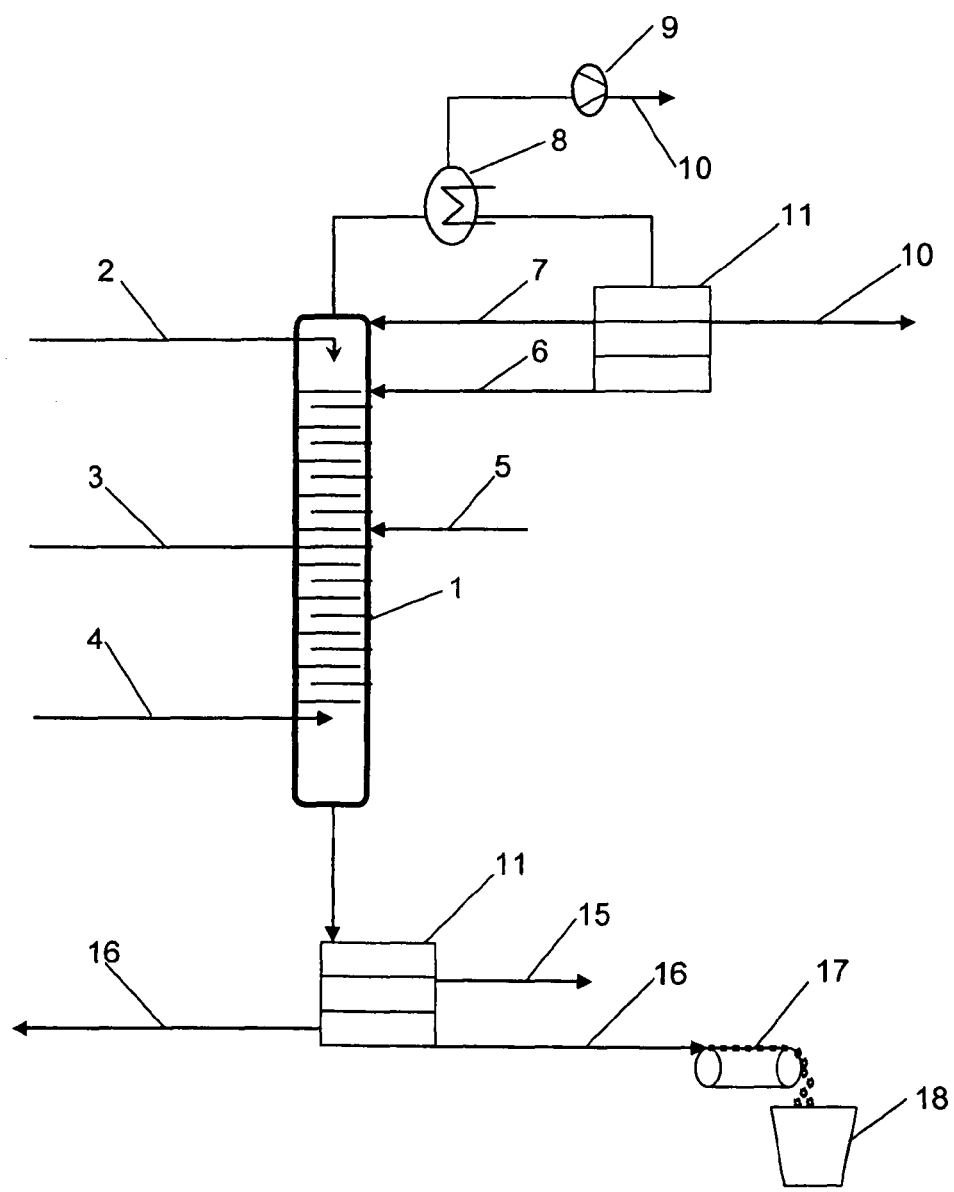
FIG. 2 depicts a simplified apparatus without stripping column. The meaning of the reference numerals is the same as in FIG. 1.

The following Examples are illustrating the implementation of the process of the invention, without any limitation being implied. The expression "steam" in each case means water vapor.

Example 1

Preparation of Acetoacetanilide

A distillation column (ID=100 mm) with 35 slit plates ("slit tray", Kühni A G, Allschwil, Switzerland) was started up with water under partial vacuum (220 mbar head pressure) as follows:
Central steam feed (below plate No. 17): 6 kg/h
Bottom steam feed: 6 kg/h
The column operated under total reflux.

After stabilization of the pressure drop (65-70 mbar) and the temperature profile (65-70° C.) feeding of aniline into the head of the column and of diketene on plate No. 14 was started, whereby the feed rates were increased every 10-15 minutes in steps of approx. 1 kg/h to the following target values:

Aniline: 0.115 kmol/h (=10.7 kg/h)
Diketene: 0.117 kmol/h (=9.83 kg/h)

At the same time the upper (below plate No. 17) steam feed was reduced in simultaneous steps of approx. 0.5 kg/h each to eventual 1 kg/h. In addition, water was fed on plate No. 14 at 3 kg/h in order to secure the availability of enough water in the reaction zone for dissipating the heat of reaction during the start-up period. The increase in column loading was compensated by reducing the bottom steam feed rate to 3 kg/h.

Once the target values of the feed rates had been reached and the column had acquired a steady state (pressure drop 70-75 mbar, temperature 60-70° C.), the acetoacetanilide melt collecting at the column bottom was separated from excess water in a phase separator and solidified on a drum flaker. The product was obtained in form of water-moist white flakes having an acetoacetanilide content of 90% and a water content of 10%. The total amount of all byproducts not resulting from starting material impurities was less than 0.05 area percent (HPLC).

Example 2

Preparation of Acetoacet-m-xylidide

A distillation column (ID=100 mm) with 17 slit plates of the same design as in Example 1 (reaction column) was fed with steam (6 kg/h) from the bottom and with water (6 kg/h) on plate No. 14 under partial vacuum (370 mbar head pressure).

Simultaneously, a second distillation column (ID=100 mm) with 18 slit plates of the same design (stripping column) was started up with steam (11 kg/h) under partial vacuum (370 mbar head pressure).

Both columns were operated with separate condensers and, initially, under total reflux. The first column was equipped with a distilling pot (approx. 6 L volume) for the bottom product, the overflow of which was conveyed into the head of the second column.

After the pressure drop (25-35 mbar) and the temperature profile (75-81° C.) had stabilized in both columns, m-xylidine (2,4-dimethylaniline; 6.4 kg/h) and diketene (4.7 kg/h) were fed into the head and on the $14^{th}$ plate, respectively, of the first column. The diketene feed was started only after the xylidine-containing reflux had reached plate No. 14. The feed rates were slowly increased while maintaining the stoichiometric ratio, until the desired performance was reached after approx. one hour:
Aniline 0.115 kmol/h(=14.0 kg/h)
Diketene 0.122 kmol/h (=10.3 kg/h)

The water feed rate on plate No. 14 was simultaneously reduced to 1.8 kg/h.

In order to remove excess diketene from the system the condensate from the second column was not recycled.

After the feed rates had reached their target values and both columns had acquired a steady state (pressure drop approx. 25-30 mbar each, temperatures 76-78° C.), the molten acetoacet-m-xylidide collecting at the bottom of the second column was conveyed through a phase separator to remove any excess water, and solidified on a drum flaker. The product was obtained in form of water-moist white flakes having a content of 92.1% acetoacet-m-xylidide and 7.7% water. Conversion (based on the m-xylidine employed) was quantitative (99.8%) within the estimated error margin (±0.5%). The excess of diketene was almost quantitatively removed with the condensate from the second column. The product contained only approx. 0.2% acetone (from diketene by hydrolysis and decarboxylation) as impurity.

Example 3

Preparation of Acetoacet-m-xylidide

A distillation column (ID=100 mm) with 22 slit plates of the design described in Example 1 (reaction column) was started up with steam (5 kg/h) under partial vacuum (355 mbar head pressure).

A second distillation column (ID=100mm) with 13 slit plates of same design (stripping column) was simultaneously started up with steam (5 kg/h) under partial vacuum (355 mbar head pressure).

Both columns were operated with separate condensers, at first under total reflux. The first column was equipped with a distilling pot (approx. 8 L volume) for the bottom product and the overflow from the distilling pot was fed into the head of the second column.

After the pressure drop (column 1: approx. 45 mbar, column 2: approx. 25 mbar) und the temperature profile (73-77° C.) had stabilized, m-xylidine (16.9 kg/h) was fed to the $2^{nd}$ plate and diketene (total 12.0 kg/h) to plate Nos. 14, 15 and 16 of the first column. The diketene feed was started only after the xylidine-containing reflux had reached plate No. 14.

Part of the condensate of the first column was withdrawn (approx. 1 kg/h) in order to prevent accumulation of the acetone present in the diketene. The condensate from the second column was not recycled, in order to remove excess diketene from the system.

Once the columns had acquired a steady state (pressure drop: in $1^{ST}$ column approx. 50 mbar, in $2^{nd}$ column approx. 25-30 mbar; temperature: 74-77° C. each), the acetoacet-m-xylidide melt collecting at the bottom of the second column was separated from excess water in a phase separator and solidified on a drum flaker. The product was obtained in form of water-moist white flakes having a content of 91.5% acetoacet-m-xylidide und approx. 8.5% water. Conversion (based on the m-xylidine employed) was quantitative (100%) within the estimated error margin (±0.8%). Excess diketene was almost quantitatively removed with the condensate of the second column. The product contained merely approx. 0.1% acetone (from diketene through hydrolysis and decarboxylation).

The invention claimed is:

1. A continuous process comprising continuously manufacturing an arylamide of acetoacetic acid from diketene and a primary or secondary aromatic amine, the reaction of the diketene with the aromatic amine is conducted in the presence of water in the manner of a reactive distillation.

2. The process of claim 1, wherein the arylamide of acetoacetic acid has the formula:

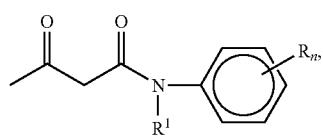

(I)

wherein $R^1$ is hydrogen or $C_{1-6}$-alkyl, n is an integer from 0 to 5, and the substituents R, if present, are independently selected from the group consisting of $C_{1-6}$-alkyl, $C_{1-6}$-alkoxy, and halogens, and is prepared from the diketene and the primary or secondary aromatic amine having the formula:

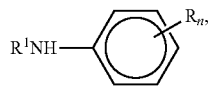

(II)

wherein $R^1$, n and R are as defined above.

3. The process of claim 2, wherein $R^1$ is hydrogen.

4. The process of claim 3, where n is an integer from 0 to 3, and the substituents R, if present, are independently selected from the group consisting of $C_{1-4}$-alkyl, $C_{1-4}$-alkoxy and chlorine.

5. The process of claim 4, wherein the reactive distillation is performed under reduced pressure.

6. The process of claim 5, wherein the reaction is performed in at least one plate column and the arylamide of acetoacetic acid is obtained as bottom product.

7. The process of claim 6, wherein the process is conducted in two columns, whereby the reaction takes place in one column and the bottom product of that column is freed from excess starting materials and volatile impurities by stripping with water vapor in a second column, the stripped bottom product is liquid.

8. The process of claim 7, wherein the stripped liquid bottom product, after removal of a separated aqueous phase, is solidified in form of flakes, pastilles or prills.

9. The process of claim 2, wherein n is an integer from 0 to 3, and the substituents R, if present, are independently selected from the group consisting of $C_{1-4}$-alkyl, $C_{1-4}$alkoxy, and chlorine.

10. The process of claim 2, wherein the reactive distillation is performed under reduced pressure.

11. The process of claim 2, wherein the reaction is performed in at least one plate column and the arylamide of acetoacetic acid is obtained as bottom product.

12. The process of claim 2, wherein the process is conducted in two columns, whereby the reaction takes place in one column and the bottom product of that column is freed from excess starting materials and volatile impurities by stripping with water vapor in a second column, the stripped bottom product is liquid.

13. The process of claim 2, wherein the reaction takes place in one column, bottom product of that column is freed from excess materials and volatile impurities by stripping with water vapor in a second column, the stripped bottom product is liquid, and the stripped liquid bottom product, after removal of a separated aqueous phase, is solidified in form of flakes, pastilles or prills.

14. The process of claim 1, wherein the reactive distillation is performed under reduced pressure.

15. The process of claim 1, wherein the reaction is performed in at least one plate column and the arylamide of acetoacetic acid is obtained as bottom product.

16. The process of claim 1, wherein the process is conducted in two columns, whereby the reaction takes place in one column, and bottom product of that column is freed from excess starting materials and volatile impurities by stripping with water vapor in a second column, the stripped bottom product is liquid.

17. The process of claim 1, wherein the reaction takes place in one column, bottom product is freed from excess materials and volatile impurities by stripping with water vapor in a second column, the stripped bottom product is liquid, and the stripped liquid bottom product, after removal of a separated aqueous phase, is solidified in form of flakes, pastilles or prills.

18. A continuous process comprising continuously manufacturing an arylamide of acetoacetic acid from diketene and a primary or secondary aromatic amine, the reaction of the diketene with the aromatic amine is conducted in the presence of water in the manner of a reactive distillation, where the chemical reaction in liquid phase and a thermal mass transfer between the liquid phase and a countercurrent vapor phase take place simultaneously.

* * * * *